(12) United States Patent
Hanson et al.

(10) Patent No.: US 9,056,129 B2
(45) Date of Patent: Jun. 16, 2015

(54) PRECISION-GUIDED NANOPARTICLE SYSTEMS FOR DRUG DELIVERY

(75) Inventors: Robert N. Hanson, Newton, MA (US); Mansoor Amiji, Attleboro, MA (US); Volkmar Weissig, Peoria, AZ (US)

(73) Assignee: Northeastern University, Boston, MA (US)

( * ) Notice: Subject to any disclaimer, the term of this patent is extended or adjusted under 35 U.S.C. 154(b) by 993 days.

(21) Appl. No.: 12/526,297

(22) PCT Filed: Feb. 11, 2008

(86) PCT No.: PCT/US2008/001766
§ 371 (c)(1),
(2), (4) Date: Aug. 7, 2009

(87) PCT Pub. No.: WO2008/147481
PCT Pub. Date: Dec. 4, 2008

(65) Prior Publication Data
US 2010/0260676 A1    Oct. 14, 2010

Related U.S. Application Data

(60) Provisional application No. 60/900,604, filed on Feb. 9, 2007.

(51) Int. Cl.
| A61K 9/14 | (2006.01) |
| A61K 49/00 | (2006.01) |
| A61K 9/51 | (2006.01) |
| A61K 47/48 | (2006.01) |
| A61K 51/12 | (2006.01) |
| B82Y 5/00 | (2011.01) |

(52) U.S. Cl.
CPC ............... *A61K 49/0002* (2013.01); *A61K 9/51* (2013.01); *A61K 47/48861* (2013.01); *A61K 47/48884* (2013.01); *A61K 51/1244* (2013.01); *B82Y 5/00* (2013.01)

(58) Field of Classification Search
CPC ........................................................ A61K 9/51
See application file for complete search history.

(56) References Cited

U.S. PATENT DOCUMENTS

| 5,607,834 | A | 3/1997 | Bagwell |
| 5,939,390 | A * | 8/1999 | Flodgaard et al. ............. 514/1.4 |
| 6,204,288 | B1 | 3/2001 | Pershadsingh et al. |
| 6,264,914 | B1 * | 7/2001 | Klaveness et al. ........... 424/1.65 |
| 6,361,944 | B1 | 3/2002 | Mirkin et al. |
| 6,541,462 | B1 | 4/2003 | Modrak |
| 6,841,193 | B1 | 1/2005 | Yang et al. |
| 6,974,706 | B1 | 12/2005 | Melker et al. |
| 2005/0175584 | A1 | 8/2005 | Paciotti et al. |
| 2006/0094674 | A1 | 5/2006 | Neel et al. |
| 2006/0246524 | A1 * | 11/2006 | Bauer et al. .................. 435/7.92 |
| 2006/0251726 | A1 * | 11/2006 | Lin et al. ....................... 424/489 |

* cited by examiner

*Primary Examiner* — Paul Dickinson
(74) *Attorney, Agent, or Firm* — Posternak Blankstein & Lund LLP

(57) ABSTRACT

A method of preparing multifunctionalized nanoparticles involves using a modular system of half-linkers to attach functional moieties that serve to deliver the nanoparticles to a desired target, exert an effect at the target, or track the nanoparticles within a cell or an animal. The modular chemistry of the half-linker system permits the custom design and synthesis of functionalized nanoparticles bearing multiple groups and therefore results in precise delivery to desired cell types and intracellular locations. The functionalized nanoparticles can be used to treat or diagnose a variety of medical conditions, including neoplastic diseases, infectious diseases, and chronic diseases.

26 Claims, 9 Drawing Sheets

PRECISION-GUIDED NANOPARTICLE SYSTEMS FOR DRUG DELIVERY

CROSS REFERENCE TO RELATED APPLICATIONS

This application claims the benefit of U.S. Provisional Application No. 60/900,604, titled "Precision-Guided Nanoparticle Systems For Drug Delivery," filed Feb. 9, 2007, the entire contents of which are incorporated herein by reference.

STATEMENT REGARDING FEDERALLY SPONSORED RESEARCH OR DEVELOPMENT

This invention was made with support from Grant #0504331 sponsored jointly by the National Science Foundation and the National Institutes of Health. The U.S. Government may have certain rights in the invention.

BACKGROUND OF THE INVENTION

The use of nanoparticles to deliver diagnostic and therapeutic agents has attracted significant interest. See, e.g., Nie, S., et al., Nanotechnology applications in cancer, Annual Review of Biomedical Engineering, 2007, 9, 257-288; Wang, M., et al., Nanotechnology for targeted cancer therapy, Expert Review of Anticancer Therapy, 2007, 7, 833-837; Haley, B., et al., Nanoparticles for drug delivery in cancer treatment, Urologic Oncology: Seminars and Original Investigations, 2008, 26, 57-64; and Vijayaraghavalu, S., et al., Nanoparticles for delivery of chemotherapeutic agents to tumors, Current Opinion in Investigational Drugs, 2007, 8, 477-484. Colloidal gold and other types of nanoparticles are particularly promising materials for the intracellular delivery of biologically active compounds in vitro and in vivo. See Love, J. C., et al., Self-assembled monolayers of thiolates on metals as a form of nanotechnology, Chemical Reviews, 2005, 105, 1103-1169; and Mukherjee, P., et al., Gold nanoparticles bearing functional anticancer drug and anti-angiogenic agent: A ["2 in 1"] system with potential application in cancer therapeutics, Journal of Biomedical Nanotechnology, 2005, 1:224-228. The feasibility of nanoparticles for drug delivery has been demonstrated in mice and in humans using thiol-derivatized PEG and recombinant human tumor necrosis factor (TNF) bound to the surface of gold nanoparticles. Paciotti, G. F., et al., Colloidal Gold: A Novel Nanoparticle Vector for Tumor Directed Drug Delivery, Drug Delivery, 2004, 11:169-183. Following intravenous injection, the PEG-AuNP-TNF particles accumulated in colon cancer tumors with much less localization in the reticulo-endothelial system or other organs. Nanoparticles bearing folate or RGD moieties have also demonstrated tumor cell localizing properties. Santra, S., et al., Folate conjugated fluorescent silica nanoparticles for labeling neoplastic cells, Journal of Nanoscience and Nanotechnology 2005, 5:899-904. Nanoparticles functionalized with mitochondriotropic ligands enter the mitochondria of living cells, thereby demonstrating the feasibility of targeting the mitochondria with nanoparticles. See D'Souza, G. G. M., et al., Nanoparticulate carriers for drug and DNA delivery to mammalian mitochondria, Pharmakeutike, 2006, 19, 110-121; and Boddapati, S., et al. Mitochondriotropic liposomes, Journal of Liposome Research, 2005, 15, 49-58.

A major issue associated with targeted nanoparticles involves control over their surface composition, i.e., the number and types of attached targeting groups or effector groups. Essentially three approaches have been used for metal nanoparticles: synthesis of a mixture of functionalized thiols for co-absorption, insertion of thiols into the available sites on a preformed surface, and modification of terminal functional groups on a preformed surface. Love et al., supra, and Fleming, M. S., et al., Stability and exchange studies of alkanethiol monolayers on gold-nanoparticle-coated silica microspheres, Langmuir, 2001, 17, 4836-4843. The latter approach typically uses a terminal amino, hydroxyl or carboxyl moiety to attach a targeting unit. More recent examples have used other terminal moieties, including maleimides, alkenes, azides, and alkynes. Houseman, B. T., et al., Maleimide-functionalized self-assembled monolayers for the preparation of peptide and carbohydrate biochips, Langmuir, 2003, 19, 1522; Lee, J. K., et al., Reactivity of vinyl-terminated self-assembled monolayers on gold: olefin cross-metathesis reactions, Langmuir, 2003, 19, 8141-8143; Collman, J. P., et al., "Clicking" functionality onto electrode surfaces, Langmuir, 2004, 20, 1051-1053; Lee, J. K., et al., Reactivity of acetylenyl-terminated self-assembled monolayers on gold: triazole formation, Langmuir, 2004, 20, 3844-3847. Because there is only a single type of terminal group, this approach relies on sequential statistical ligations to introduce the targeting groups. Hong, S., et al., The binding avidity of a nanoparticle-based multivalent targeted drug delivery platform, Chemistry and Biology, 2007, 14, 107-115. This approach depends upon having the appropriate functional groups in the targeting unit. As a result, there is variability in the ligation efficiency. The bioconjugation reaction itself may significantly reduce the biological activity of the targeting unit, depending upon its mechanism of action or its binding site. Using the methodology of the prior art, it is difficult to introduce multiple functional units onto the surface of the nanoparticles in reproducible ratios. Thus, there remains a need for new technology to attach multiple targeting and effector groups onto nanoparticles to permit their precise delivery and biological action.

BRIEF SUMMARY OF THE INVENTION

The invention provides methods for making targeted functionalized nanoparticles, compositions containing the functionalized nanoparticles, and methods of using them to diagnose and treat disease. The nanoparticles can be derivatized with multiple agents in predictable and reproducible ratios to provide chemical or biological effector agents for treatment of a variety of diseases as well as to provide tracking and targeting modalities. The nanoparticles can be precisely guided to intracellular targets where a drug or biological agent can exert its effect. The power and flexibility of the multifunctionalized nanoparticles of the invention derive from the ability to couple multiple targeting and effector moieties to each nanoparticle using a modular linkage chemistry.

One aspect of the invention is a method of preparing a set of functionalized nanoparticles having the advantageous properties described above. In step (a) the nanoparticles and reagents needed to derivatize them are provided, including a plurality of nanoparticles, a set of first half-linkers, a set of second half-linkers, and a set of functional moieties. The first half-linkers each possess a first reactive group and a second reactive group, and the second half-linkers each possess a third reactive group and a fourth reactive group. The set of functional moieties includes two or more different types of functional moiety, which can be, e.g., a tracking moiety, a delivery moiety, or an effector moiety. The set of first half-linkers includes two or more different types of second reactive group, and the set of second half-linkers includes two or more different types of third reactive group. Each type of second reactive group reacts with essentially only one type of third reactive group to form a cross-reacting pair capable of joining a certain type of first half-linker with a certain type of second half-linker. In step (b), the plurality of nanoparticles are reacted with the first reactive groups in the set of first half-linkers. In step (c), the fourth reactive groups on the set of second half-linkers are reacted with a set of functional moieties. In some embodiments, the fourth reactive group is dispensed with, and the second half linker is merely a derivative of the functional moiety having a third reactive group for reacting with the second reactive group of the first half-linker. In step (d), the second reactive groups of the set of first half-linkers from step (b) are reacted with the third reactive groups of the set of second half-linkers from step (c) to form the set of functionalized nanoparticles. In some embodiments, the reaction of step (c) is performed separately for each different functional moiety. In some embodiments, the reaction of step (d) is performed using one type of cross-linking pair of second and third reactive groups at a time; in other embodiments, two or more cross-linking pairs are coupled simultaneously.

In yet another aspect of the invention, another method is provided for preparing a set of functionalized nanoparticles. In step (a) of the method, the nanoparticles and reagents needed to derivatize them are provided. The nanoparticles as provided are covalently bound to a set of first half-linkers through a first reactive group of the first half-linkers, and each of the first half-linkers also contains a second reactive group. Each of the provided second half-linkers is covalently bound to a functional moiety, which is either a tracking moiety, a delivery moiety, or an effector moiety. The second half-linkers also contain third reactive groups, each type of which react with essentially only one type of second reactive group. In step (b) of the method, the second and third reactive groups are reacted to form the set of functionalized nanoparticles.

Another aspect of the invention is a method of preparing a set of functionalized nanoparticles. In step (a) of the method, the nanoparticles and reagents needed to derivatize them are provided. The nanoparticles as provided are covalently bound to a set of first half-linkers through a first reactive group of the first half-linkers, and each of the first half-linkers also contains a second reactive group. A provided set of second half-linkers each possess a third reactive group and a fourth reactive group. The set of first half-linkers comprises two or more different types of second reactive group and the set of second half-linkers comprises two or more different types of third reactive group, each type of second reactive group reacting with essentially only one type of third reactive group to form a cross-reacting pair. In step (b), the fourth reactive groups of the set of second half linkers are reacted with two or more different types of user-supplied functional moiety, the functional moieties being either a tracking moiety, a delivery moiety, or an effector moiety. In step (c) the second and third reactive groups are reacted to form the set of functionalized nanoparticles.

Still another aspect of the invention is a set of functionalized nanoparticles for the diagnosis or treatment of a medical condition. Each functionalized nanoparticle of the set comprises a plurality of functional moieties, each of which is attached to the nanoparticle via a specialized linker. The linker includes a first half-linker and a second half-linker. The first half-linker is covalently bound to the nanoparticle and to the second half-linker, while the second half-linker also is covalently bound to the functional moiety. Each nanoparticle of the set comprises two or more different functional moieties, such as a tracking moiety, a delivery moiety, and an effector moiety. The tracking moiety can be used to follow the uptake and distribution of the nanoparticles in a cell, an animal, or a patient, for example through providing a label that can provide an image of the nanoparticle distribution. The delivery moiety causes the nanoparticles to localize in a chosen organ, cell, or cell compartment, or to remain in the circulation for an extended period of time. The effector moiety is a chemical or biological agent that carries out a desired end effect of the nanoparticles, such as triggering cell death, or activating or inhibiting a receptor, an enzyme, or a gene. Preferably the effector moiety is a receptor ligand selected from an estrogen receptor antagonist, an androgen receptor antagonist, folic acid, an RGD peptide, and tumor necrosis factor. In certain embodiments, the different functional moieties are present on the nanoparticles in a composition stoichiometry that is nearly constant over the set, with the variance of the stoichiometry over the set being less than 5%.

Yet another aspect of the invention is a method of treating a medical condition. The method includes administering the set of functionalized nanoparticles described above to a subject.

Another aspect of the invention is a method of diagnosing a medical condition. The method includes administering the set of functionalized nanoparticles described above to a subject and monitoring the results.

Still another aspect of the invention is a method of delivering a chemical or biological agent to a cell. The method includes contacting the cell with the set of functionalized nanoparticles described above.

In another aspect, the invention provides a kit for preparing a set of functionalized nanoparticles. The kit includes a plurality of nanoparticles that are covalently bound to a set of first half-linkers through a first reactive group of the first half-linkers. Each first half-linker also includes a second reactive group. The kit further includes a set of second half-linkers, each of which is covalently bound to one of a set of functional moieties; the functional moieties can be a tracking moiety, a delivery moiety, or an effector moiety. Each second half-linker also includes a third reactive group. The set of first half-linkers includes two or more different types of second reactive group, and the set of second half-linkers includes two or more different types of third reactive group. Each type of second reactive group reacts with essentially only one type of third reactive group to form a cross-reacting pair.

A further aspect of the invention is another kit for preparing a set of functionalized nanoparticles. The kit includes a plurality of nanoparticles that are covalently bound to a set of first half-linkers through a first reactive group of the first half-linkers. Each first half-linker also includes a second reactive group. The kit also includes a set of second half-linkers, each possessing a third reactive group and a fourth reactive group. The kit further includes a set of functional moieties, each of which is either a tracking moiety, a delivery moiety, or an effector moiety. Each functional group reacts with a fourth reactive group. The set of first half-linkers includes two or more different types of second reactive group, and the set of second half-linkers includes two or more different types of third reactive group. Each type of second reactive group reacts with essentially only one type of third reactive group to form a cross-reacting pair.

Another aspect of the invention is a kit for preparing a set of functionalized nanoparticles. The kit includes a plurality of nanoparticles that are covalently bound to a set of first half-linkers through a first reactive group of the first half-linkers. Each first half-linker also includes a second reactive group. The kit also includes a set of second half-linkers, each possessing a third reactive group and a fourth reactive group that is capable of reacting with a set of user-supplied functional moieties. The set of functional moieties includes two or more different types selected from a tracking moiety, a delivery moiety, and an effector moiety. The first half-linkers include two or more different types of second reactive group, and the second half-linkers include two or more different types of third reactive group. Each type of second reactive group reacts with essentially only one type of third reactive group to form a cross-reacting pair.

BRIEF DESCRIPTION OF THE DRAWINGS

Other features and advantages of the invention will be apparent from the following description of the preferred embodiments thereof and from the claims, taken in conjunction with the accompanying drawings.

DETAILED DESCRIPTION OF THE INVENTION

The inventors have developed precision-targeted functionalized nanoparticle compositions that can be used to diagnose and treat disease. The nanoparticles are superior to conventional nanoparticles for biomedical applications because they can be functionalized through the attachment of multiple targeting and effector agents, resulting in controlled delivery to one or more intracellular targets. Precision targeting of the nanoparticles results from a new modular synthetic approach that allows attachment of a user-defined set of functional moieties in defined proportions from a modular synthetic approach such that chemical agents such as drugs or toxins as well as biological agents such as antibodies are for treatment of a variety of diseases as well as to provide tracking and targeting modalities. The nanoparticles can be precisely guided to intracellular targets where a drug or biological agent can exert its effect. The power and flexibility of the multifunctionalized nanoparticles of the invention derive from the ability to couple multiple targeting and effector moieties to each nanoparticle using a modular linkage chemistry.

Functionalized nanoparticles can be prepared by chemical derivatization of their surface. The surface of gold nanoparticles, for example, reacts with thiolated reagents, while cross-linked iron oxides can be coated with aminopropyl silyl groups to give a modifiable surface. A method of preparing functionalized nanoparticles is to apply a self-assembled monolayer of first half-linkers to the surface of the nanoparticles. The first half-linkers possess a reproducible array of chemo-orthogonal functional groups, such as, for example, azides (click chemistry), alkenes (Grubb's olefin metathesis), maleimides (Diels-Alder chemistry), alcohols (Mitsunobu reaction) and amines (peptide conjugation). The composition of this array is programmable because the initial self assembly phase is determined by the reactivity of the initial conjugating group with the metal surface (dithiols for gold and acyl groups for aminopropylsilyl protected iron oxides).

Figure 1:
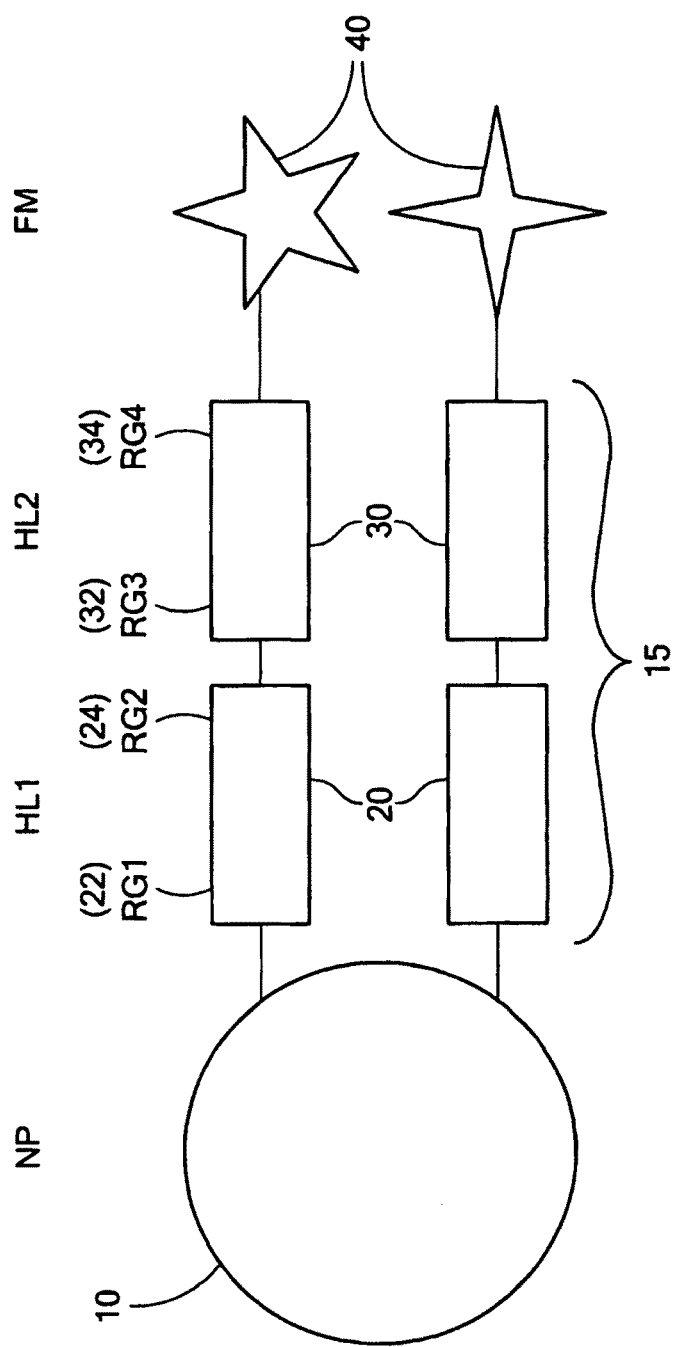
FIG. 1 is a schematic representation of a multifunctional nanoparticle according to the invention. NP represents a nanoparticle 10 that is functionalized with at least two different functional moieties (FM) (40), each attached through a linker (15) formed by the conjugation of a first half-linker (HL1) (20) and a second half-linker (HL2) (30). Each HL1 has a first reactive group (RG1) (22) that mediates attachment to the nanoparticle and a second reactive group (RG2) (24) that mediates attachment to HL2 via a third reactive group (RG3) (32). A fourth reactive group (RG4) (34) on HL2 mediates attachment to a functional group. The functionalized nanoparticle is attached to at least two different functional groups.

A set of functionalized nanoparticles according to the invention contains a plurality of nanoparticles whose surfaces have been chemically modified to attach certain chemical and/or biological agents. With reference to FIG. 1, each nanoparticle 10 is covalently attached to a plurality of linkers 15, which in turn are covalently attached to functional moieties 40. Each linker is built up from two half linkers, 20 and 30. The individual nanoparticles of the set are multi-functional, as determined by their attachment to at least two different kinds of functional moieties. This allows precise targeting. A unique characteristic of the set of nanoparticles of the present invention is that a modular system is used to couple a desired mixture of functional moieties to the nanoparticles. The modularity arises through the use of two chemically matched half-linkers for the attachment of each type of functional moiety. The complementary reactive groups of the half-linkers are selected to permit chemo-orthagonal coupling of the half-linkers. Thus, the structure and reactivity of the half-linkers, when combined in a precise ratio, effectively converts a chemically uniform nanoparticle surface into a pre-selected array of chemoselective docking sites that subsequently is converted into the desired array of targeting and effector moieties for treatment or diagnosis of disease. A set of functionalized nanoparticles according to the invention generally will include a selection of functional moieties chosen to address a common biological target or collection of targets relevant to treatment or diagnosis of the same medical condition. For example, a set of nanoparticles can contain functional moieties that act at different parts of a particular cell type, such as a particular kind of tumor cell. The attachment of two or more different functional moieties to each nanoparticle renders the nanoparticles multifunctional. Functionalized nanoparticles according to the invention are preferably biocompatible, i.e., non-toxic and non-hazardous to living cells and organisms, though for in vitro and animal studies, biocompatibility may not be required. In some embodiments, e.g., for administration to humans, the functionalized nanoparticles are also biodegradable, so that their function and presence is of limited duration.

Referring again to FIG. 1, first and second half-linkers share similarities in structure. Each is a chain from 2 to about 20 atoms in length, and each possesses two reactive groups. The first half-linker 20 is designed to attach through a first reactive group 22, which is generally at or near one end of the linker, to reactive groups at the surface of the nanoparticles. For a given type of nanoparticle, all the first reactive groups of a set generally will be the same type of chemically reactive group, one that is suitable for stable covalent coupling to the nanoparticle surface. At or near the other end of the first half-linker is a second reactive group 24, which can be varied within a set to determine, through its selective reactivity with the second half-linker, the desired mixture of functional moieties attached to each nanoparticle. Third reactive group 32, which is located at or near one end of second half-linker 30, reacts with second reactive group 24 to covalently join the first and second half-linkers. Fourth reactive group 34, which is at or near the other end of the second half-linker, is reacted with a reactive group on a functional moiety, thereby covalently linking the functional moiety to the nanoparticle.

Figure 2:
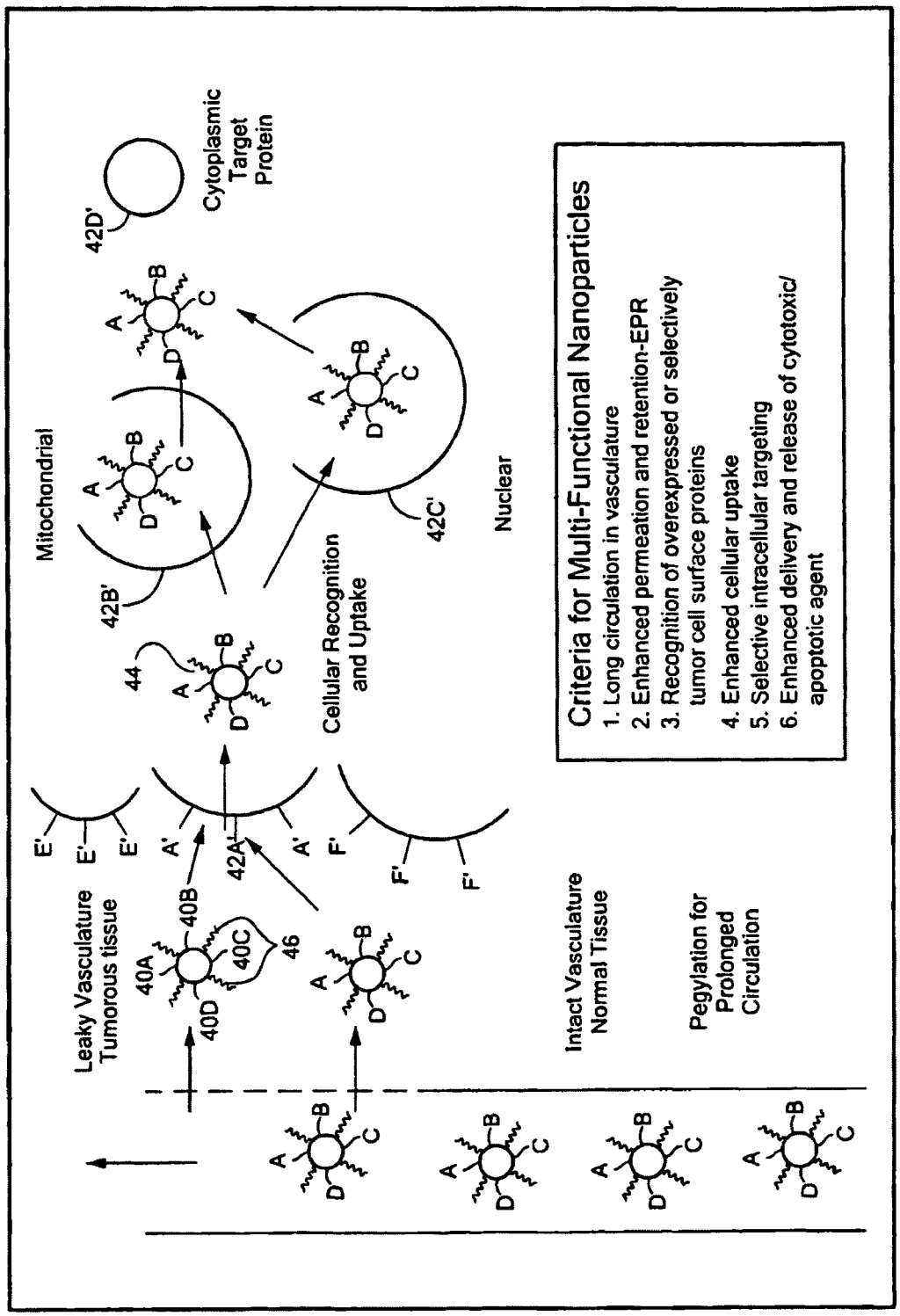
FIG. 2 illustrates a paradigm for the use of multi-functional nanoparticles to treat a tumor by means of targeting to multiple intracellular targets. The nanoparticle has attached delivery and/or effector moieties A-D and PEG (wavy lines). A'-D' represent cellular targets bound by moieties A-D, respectively.

A paradigm for using the multifunctionalized nanoparticles of FIG. 1 to treat a disease, such as cancer, is shown in FIG. 2. Functional moieties 40 A-40 D are selected to provide binding to surface proteins on tumor cells, e.g., 42A', internalization within cells 44, association with selected intracellular compartments such as mitochondria 42B' and, ultimately, triggering of apoptosis or cytotoxicity 42D'. Polyethylene glycol (PEG) 46 is added to the nanoparticles to increase circulatory half-life.

Figure 3:
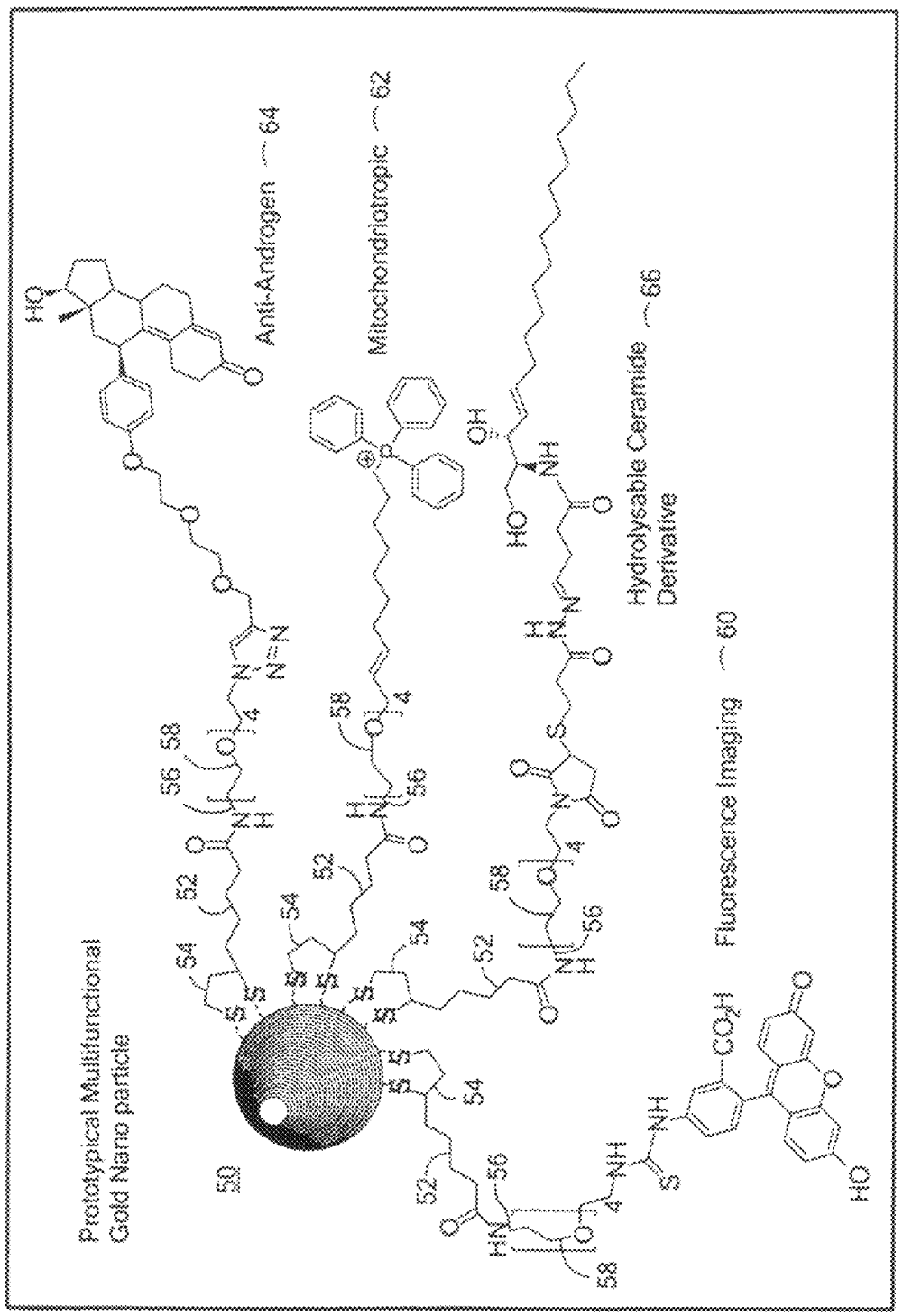
FIG. 3 shows a schematic representation of one embodiment of a multifunctional gold nanoparticle 50 designed to treat prostate cancer. The first half-linkers are lipoic acid molecules 52, which are coupled to the nanoparticle through their dithiol groups 54. The first half-linkers are coupled through amide linkages 56 to oligoethylene glycol chains 58, which serve as second half-linkers. A fluorophore 60 serves as a tracking moiety, while an alkyltriphenyl phosphonium group 62 serves as a delivery moiety that targets the nanoparticle to mitochondria. An androgen receptor antagonist 64 functions both as delivery moiety and effector moiety, and a hydrolyzable ceramide derivative 66 acts as an effector moiety by triggering apoptosis through a mitochondrial mechanism.

A prototype multifunctionalized gold nanoparticle 50 for the treatment of prostate cancer is shown in FIG. 3. An anti-androgen moiety 64 serves as a delivery moiety as well as an effector moiety, causing binding to and antagonism of androgen receptors on and within prostate cancer cells. An alkyltriphenyl phosphonium delivery moiety 62 causes the nanoparticles to become localized within the mitochondria. Release of ceramide 66 leads to activation of apoptosis. Finally, the attachment of a fluorophore 60 permits tracking of the nanoparticles within the body of an animal or a human patient.

Nanoparticles

A variety of nanoparticles are suitable for use in the methods and compositions of the invention. Suitable nanoparticles are preferably essentially spherical in form, though other forms can be used, and composed of a metal or organic (e.g., polymeric) material. The material can be homeogeneous or blended from two or more components. The surface of the nanoparticles has one or more chemically reactive groups suitable for attaching a first half-linker. Preferably, the surface of the nanoparticles contains multiple, evenly distributed reactive groups of a single type. Some non-limiting examples of nanoparticles suitable for use in the invention are listed in Table 1. Preferred metallic nanoparticles include gold, and silver nanoparticles. Preferred inorganic nanoparticles include silica nanoparticles and quantum dots. Organic nanoparticles can be, e.g., polymers derivatized to expose selected reactive groups at their surface. See, e.g., Townsend, S. A, et al., Tetanus toxin C fragment-conjugated nanoparticles for targeted drug delivery to neurons, Biomaterials (2007), 28(34), 5176-5184; Weiss, B., et al., Coupling of Biotin-(poly (ethylene glycol)) amine to Poly(D,L-lactide-co-glycolide) Nanoparticles for Versatile Surface Modification, Bioconjugate Chemistry (2007), 18(4), 1087-1094; and Gindy, M. E., et al., Functional block copolymer nanoparticles for targeted drug delivery and imaging PMSE Preprints (2006), 95:989-990. The size of the nanoparticles, e.g., the average (mean) diameter, is in the range from about 2 nm to about 100 nm; preferably the average diameter is in the range from about 5 nm to about 20 nm. The size distribution within a set of nanoparticles is preferably a normal distribution; however, for certain applications a set can have other size distributions, such as bimodal or other types of distribution. Size distribution and average diameter of the nanoparticles can be measured by any method known in the art, including but not limited to light scattering, electron microscopy, and size exclusion chromatography.

As used herein, a "set" of nanoparticles or functionalized nanoparticles refers to two or more nanoparticles that are made, stored, or used together. Generally, a set of functionalized nanoparticles will be in the form of a composition such as a liquid (e.g., aqueous) or dry suspension. A set of functionalized nanoparticles typically will be designed to diagnose or treat a selected medical condition, or a collection of related medical conditions. Sets of nanoparticles can be combined, either physically, e.g., by blending two or more suspensions of nanoparticles, or during use, e.g., by co-administration of two or more sets of nanoparticles to a subject or to cells in vitro. Where "each" or "every" nanoparticle of a set is referred to herein, it is understood that sets of nanoparticles may contain a small fraction, e.g., less than 10%, less than 5%, or less than 1% of the nanoparticles of the set, whose properties deviate from the population average properties of the set.

TABLE 1

Examples of nanoparticles for use with the invention

| Nanoparticle | Reactive Group | First Reactive Group |
|---|---|---|
| Gold | Au | Thiol |
| Cross-linked iron oxide (CLIO) | Aminopropylsilyl protecting group | Acyl |
| Silver | Ag | Amine |
| Organic polymer | COOH or $NH_2$ | $NH_2$ or COOH |
| Quantum dots | COOH | $NH_2$ |

Functional Moieties

Each functionalized nanoparticle of a set carries two or more different types of functional moieties. Functional moieties carry out the function of the nanoparticles in therapy or diagnosis, and generally belong to one of three different classes: tracking moieties, delivery moieties, or effector moieties. The two or more different types of functional moieties present on a given nanoparticle can be derived from one or more of these classes. Preferably, at least one functional moiety on a functionalized nanoparticle is a delivery moiety.

Tracking moieties can be especially useful in diagnosis, e.g., to detect, localize, image, and/or quantify certain cells or molecules that are indicative of a medical condition or of the physiological condition of a subject. Tracking moieties can also be used to evaluate the performance of functionalized nanoparticles, particularly whether they are reaching their intended biological target or targets. Tracking moieties can be used to follow and map the pharmacokinetic properties of functionalized nanoparticles, e.g., using animal studies or cell culture studies. Tracking moieties also can be employed to develop improvements, e.g., by modifying or adding delivery or effector moieties to a set of functionalized nanoparticles. Non-limiting examples of tracking moieties include fluorophores for tracking and imaging of functionalized nanoparticles in cells and tissues using fluorescence or fluorescence microscopy; stable free radicals for use with electron paramagnetic resonance, such as a 2,2,6,6-tetramethylpiperidine-1-oxyl (TEMPO) group; probes for Raman spectroscopy, such as a perdeuterated alkyl or aryl phosphonium group that will provide both tracking and delivery to mitochondria; and radioactively-labeled compounds, which can be localized or imaged with a variety of detectors, e.g., by positron emission.

A delivery moiety is one that causes functionalized nanoparticles to become specifically localized over time, usually due to binding or other interactions with specific molecules, or physical conditions such as pH or electrical potential, that are found selectively or exclusively in certain cell types, such as tumor cells, or cell compartments, such as endosomes or mitochondria. The modular linkage chemistry used to prepare functionalized nanoparticles of the invention enables a highly flexible and specific targeting mechanism to be built into the nanoparticles. For example, multiple targeting mechanisms can be incorporated into the same nanoparticle, resulting in delivery to multiple compartments or multi-stage delivery that would not be possible with only a single targeting agent. In some embodiments, for example, a ligand for a cell surface receptor is used as a first delivery moiety that leads to binding and uptake of the functionalized nanoparticles into a specific cell type, followed by a second delivery moiety such as a phosphonium compound that drives the nanoparticles into the mitochondrial matrix of the target cells. Examples of delivery moieties are provided in Table 2.

TABLE 2

Exemples of Delivery Moieties

| Target | Delivery Moiety | Targeting Characteristics |
|---|---|---|
| Mitochondria | Stearyl triphenyl phosphonium | Electrophoretic uptake |
| Cell interior | TAT peptide | Cell penetrating moiety, 11-mer |
| Endosomal pathway | Acyl hydrazone | pH-sensitive linker |
| Androgen receptor | Androgen antagonist | Receptor binding |

Effector moieties are largely responsible for carrying out the end effects of functionalized nanoparticles. They can be, for example, chemical or biological agents such as enzyme inhibitors or activators, toxins, triggers of apoptosis, receptor agonists or antagonists, antibodies, or activators or inhibitors of gene transcription, gene regulation, or protein expression. Non-limiting examples of effector moieties are shown in Table 3. It is understood that the function of effector moieties and delivery moieties can overlap. Thus, in some instances the same agent could be considered to be either a delivery moiety, an effector moiety, or both. Two or more effector moieties can be coupled to the same nanoparticle; a combinatorial approach can enhance the specificity and/or potency of functionalized nanoparticles. The effector moiety or moieties for a set of functionalized nanoparticles are generally chosen to act on one or more molecular or cellular targets involved in the medical condition that the functionalized nanoparticles are intended to treat or diagnose.

TABLE 3

Exemples of Effector Moieties and Their Biological Targets

| Biological Target | Effector Moiety | Reactive Group on Effector Moiety | Type of Interaction |
|---|---|---|---|
| Estrogen receptor | ER antagonist, e.g., 17α-ethynyl estradiol | 17α-ethynyl, 11β-oligoethylene glycol, 11β-4-hydroxyphenyl | Ligand-receptor |
| Androgen receptor | AR antagonist, e.g., 17α-ethynyl testosterone, 11β-progargyloxyethyloxyphenyl norandrostadiene | 17α-ethynyl | Ligand-receptor |
| Folate receptor | Folic acid | Glutamic acid component | Ligand-receptor |
| Integrin receptor | RGD peptide | Pendant groups on linear or cyclic RGD derivatives or nonpeptidyl analogs | Ligand-receptor |
| VEGF receptor | Tyrosine kinase inhibitor | Ethynyl group | Enzyme inhibitor |
| EGF receptor | Tyrosine kinase inhibitor (e.g., Tarceva, Iressa, Tykerb) | Ethynyl at 3 position of 4-anilino moiety of Tarceva | Enzyme inhibitor |
| Tumors | Tumor necrosis factor (TNF) | COOH | Ligand-receptor |

TABLE 3-continued

Examples of Effector Moieties and Their Biological Targets

| Biological Target | Effector Moiety | Reactive Group on Effector Moiety | Type of Interaction |
|---|---|---|---|
| Mitochondria | Ceramide, Betulinic acid, Lonidamine | 6-position of ceramide | Induce apoptosis |

Methods of Preparing Functionalized Nanoparticles

Functionalized nanoparticles according to the invention are prepared using a modular strategy in which two half-linkers are used to couple the surface of the raw nanoparticles to two or more different functional moieties. Such nanoparticles can be prepared using different variations of a basic strategy.

The first step in producing functionalized nanoparticles is to provide the required materials. These materials include: (i) the raw nanoparticles; (ii) a set of first half-linkers; (iii) a set of second half-linkers; and a set of functional moieties.

Suitable nanoparticles are described above. Factors in selecting nanoparticles include their average diameter and size distribution, their surface chemistry, and in some applications their biocompatibility as well as their biodegradability. If suitable reactive groups are not available on the surface of the raw nanoparticles, then the surface can be derivatized or coated to provide such reactive groups. Since the modularity of the present functionalized nanoparticles arises through the ability to couple different first half-linkers with different second half-linkers, only a single type of reactive group is required at the surface of the nanoparticles. So as to prevent steric interactions among the linkers and functional groups, the nanoparticle reactive groups should be evenly distributed over the surface of each particle.

Figure 5:
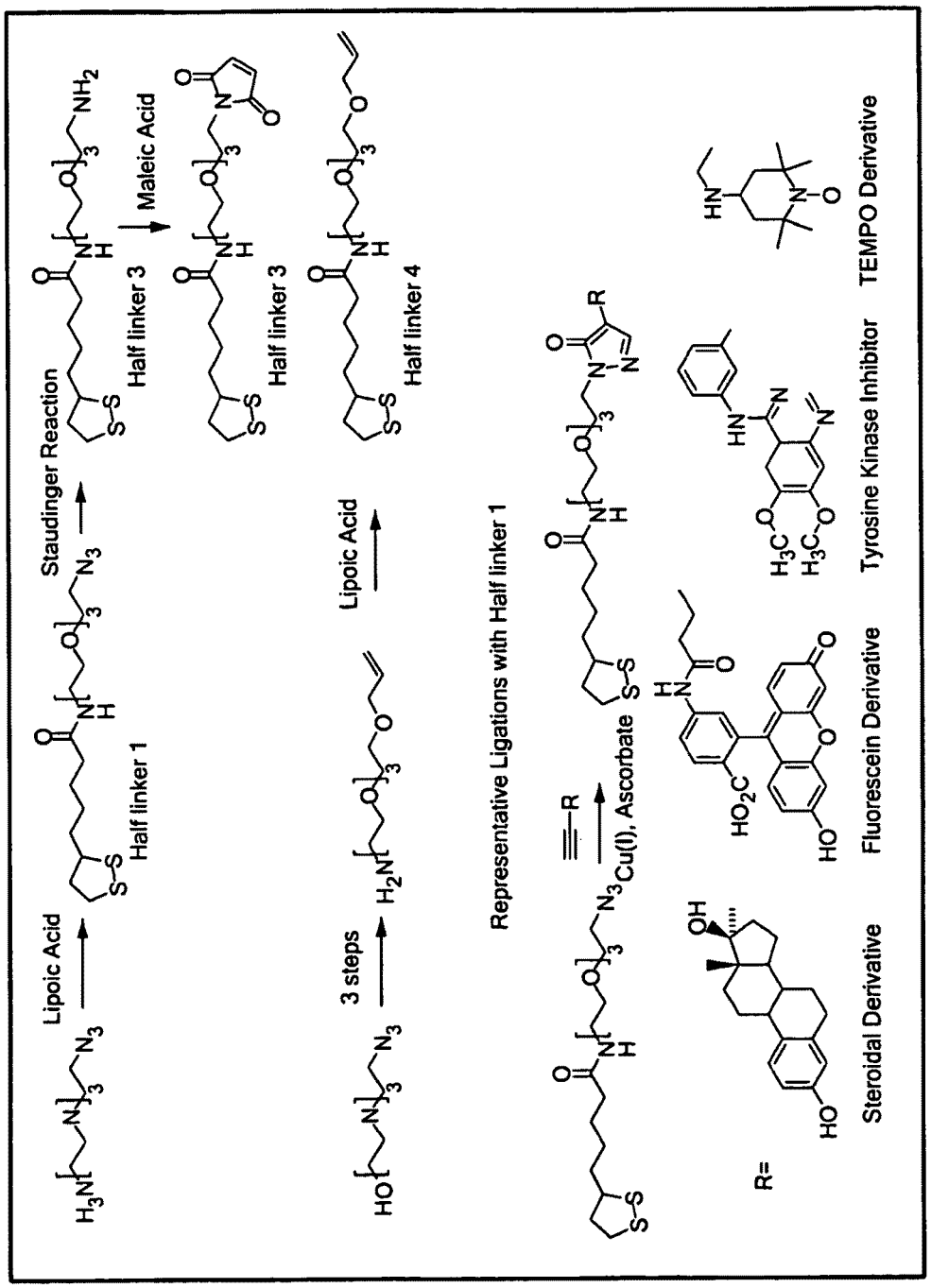
FIG. 5 depicts several embodiments of the first half-linker (Half linker 1-4) and their synthesis (upper portion of the figure). The reaction of first half-linker 1, having $N_3$ as the second reactive group, with an assortment of second half-linkers, having an alkyne as the third reactive group, is also depicted (lower portion of the figure). Examples of functional groups (R) are shown at the bottom of the figure.
Figure 6:
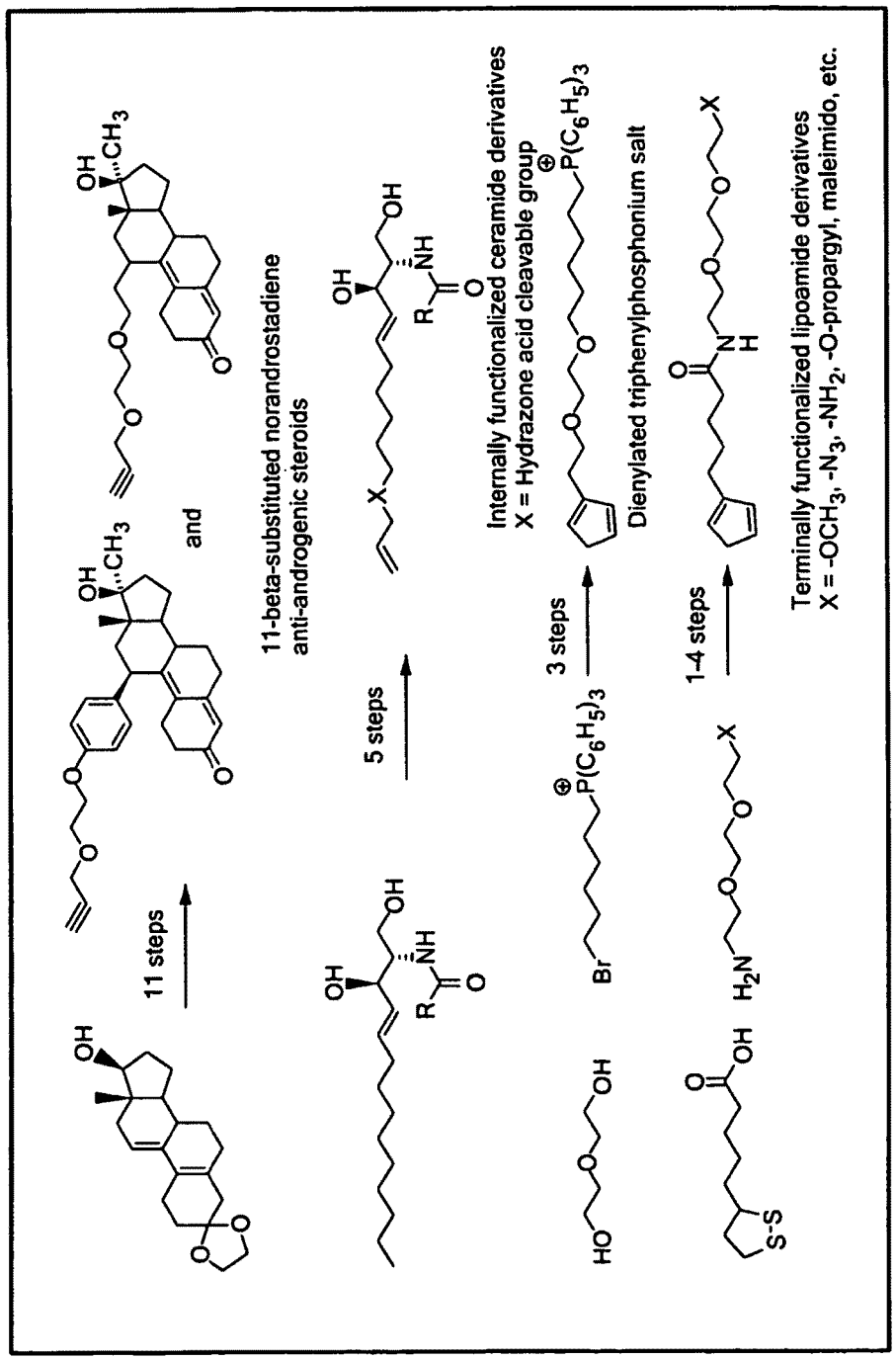
FIG. 6 shows schematic representations of several embodiments of the synthesis of second half-linkers conjugated to functional groups, and a first half-linker having various second reactive groups (bottom of the figure).

The first half-linkers each have a first reactive group disposed at or near one end of the half-linker and a second reactive group disposed at or near the other end. The first reactive group is chosen to be capable of reacting with the available reactive groups on the surface of the nanoparticles. The first reactive group also determines the strength of attachment of the functional moieties to the nanoparticles. Strong covalent binding is preferable, to prevent loss of payload during handling and biodelivery. For example, the use of dithiols or trithiols as the first reactive group for gold nanoparticles yields an attachment site with the strength of two or three covalent bonds per linker, providing greater stability than a single covalent bond. The second reactive group is chosen to be capable of cross-reacting with a second half-linker. The set of first half-linkers used to form a set of functionalized nanoparticles includes two or more different types of first half-linker which differ in their second reactive groups. Each of those second reactive groups will react selectively with a different second half-linker. Therefore, the set of first half-linkers will be capable of reacting with two or more different second half-linkers. Some non-limiting examples of first half-linkers are shown in Table 4. Synthetic schemes for preparing several exemplary first half-linkers, as well as functional moieties, are shown in FIGS. 5 and 6.

TABLE 4

Examples of First Half-linkers

| Nanoparticle | First Half-Linker | First Reactive Group | Second Reactive Group |
|---|---|---|---|
| Gold | Lipoic acid | Dithiol | Oligoethylene glycol modified to: |
| | Lipoamide | Dithiol | Azide |
| | Asparagusic acid | Dithiol | Alkene |
| | trimercaptomethyl derivative | Trithiol | Maleimide |
| | | | Amine (t-Boc) |
| Cross-linked iron oxide (CLIO) (aminopropylsilyl-protected) | Acyl | Acyl | Monoamidoglutaric acid modified to: Azide Alkene Maleimide Amine (t-Boc) |
| Quantum dots | Same as for Gold | Same as for gold | Same as for gold |

The second half-linkers each have a third reactive group disposed at or near one end of the half-linker and a fourth reactive group disposed at or near the other end. The third reactive group is chosen to be capable of reacting with the available second reactive groups on the first half-linkers. The fourth reactive group is selected to be reactive with available reactive groups on the desired functional moieties. The set of second half-linkers used to form a set of functionalized nanoparticles includes two or more different types of second half-linker which differ in their third reactive groups; they may or may not also differ in their fourth reactive groups. The different third reactive groups in a set are chosen to be complementary to the set of second reactive groups for the same set of functionalized nanoparticles. That is, each third reactive group of the set will react only with one out of the set of second reactive groups; the reactions between second and third reactive groups are chemo-orthogonal, i.e., each type of second reactive group reacts with only one type of third reactive group, and vice versa. In this way, the composition stoichiometry of different functional moieties on a functionalized nanoparticle, and within a set of functionalized nanoparticles, is determined by the stoichiometry of first half-linkers used to react with the nanoparticle surface.

Figure 4:
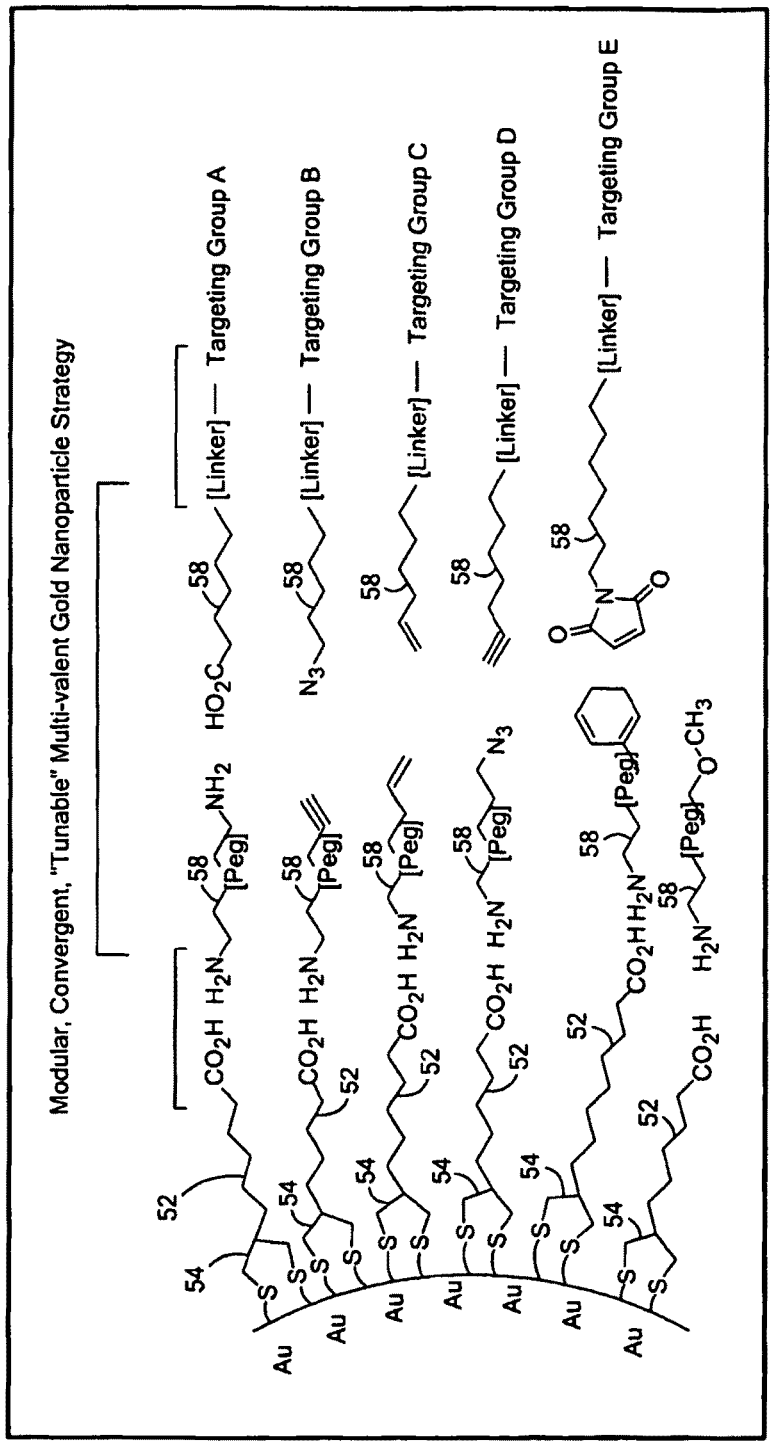
FIG. 4 illustrates an embodiment of the modular linkage chemistry for assembling first half-linkers to selected second half-linkers bound to different targeting groups. The first half-linkers (20) (left side of diagram) are formed from lipoic acid groups (52) joined via a peptide linkage to variously derivatized oligoethylene glycol (OEG) (58) chains. The dithiol (54) of lipoic acid serves as the first reactive group, while the various groups attached to the right-hand side of the OEG chains provide an assortment of second reactive groups. Second half-linkers (right side of diagram) are formed from OEG chains derivatized with various third reactive groups chosen to react specifically with matching second reactive groups, as aligned. The second half-linkers are coupled through fourth reactive groups (not shown) to functional moieties (Targeting Groups A-E).

In order to permit the attachment of multiple functional moieties, which improves the precision targeting and potency of the nanoparticles, it is useful to have a large set of second and third reactive groups that maintain chemo-orthogonality within the set, i.e., a large set of reactive groups within which complementary pairs of second and third reactive groups react essentially exclusively. It is understood that while these reactions are selective, they are not absolutely selective, and some amount of undesired cross-reactivity may occur. Preferably, the amount of undesired second and third reactive group cross-reactivity is minimal, such as less than 10%, less than 5%, or less than 1% of the final product. One example of a chemo-orthogonal set of second and third reactive groups is shown in Table 5. A similar set is illustrated in FIG. 4. The average skilled artisan can add other members to these sets, or prepare additional sets as required.

TABLE 5

Sample Set of Chemo-Orthogonal Reactive Groups

| Second Reactive Group | Third Reactive Group | Chemical Reaction |
|---|---|---|
| azide | alkyne | to join half-linkers Huisgen [3 + 2] cycloaddition |
| alkene | alkene | Grubb's olefin metathesis |
| maleimide | dienyl or thiol | Diels-Alder or thiol chemistry |
| alcohol | phenol | Mitsunobu reaction |
| amine | carboxylic acid | Peptide conjugation |

The order of the first reaction steps to prepare a set of functionalized nanoparticles generally is not critical; however, the final reaction step will ordinarily be the coupling of the first and second half-linkers through the second and third reactive groups. Prior to that key reaction, the nanoparticles can be reacted with the first reactive groups of the first half-linkers and the functional moieties can be reacted with the fourth reactive groups of the second half linkers in any order desired. Further details of the reaction steps can be found in the examples provided below.

Kits

One or more of the components needed for preparing functionalized nanoparticles according to the invention may be conveniently provided in the form of a kit. A kit will optionally include instructions for use of the components to prepare functionalized nanoparticles according to a method of the invention, as well as one or more reagents useful in carrying out any of the coupling, blocking, or unblocking reactions. A kit may also include packaging materials.

For example, a kit can include a plurality of raw or pre-treated nanoparticles for reaction with a first half-linker. A kit can include nanoparticles of different materials or different sizes, for selection by the user. A kit can include a plurality of first half-linkers. A kit can include a plurality of second half-linkers. First and second half-linkers can be supplied either singly or in cross-reacting pairs. Sets of first and second half-linkers can also be supplied in which different types of first half-linker and second half-linker are present, but each half-linker type reacts selectively only with a complementary half-linker type. A kit can also include one or more functional moieties, or it can omit the functional moieties, leaving them to be supplied by the user.

In one embodiment, a kit includes a plurality of nanoparticles, a first half-linker, a second half-linker, and a functional group for assembly by the user, either alone or together with user-supplied components. In another embodiment, a kit includes a plurality of nanoparticles that are already derivatized with one or more first half-linkers. The first half-linkers can include two or more different types, e.g., differing in their second reactive groups, each first half-linker attached in a pre-determined stoichiometry with respect to the remaining types. In yet another embodiment, a kit includes a plurality of nanoparticles already derivatized with one or more types of first half-linker, as well as a set of second half-linkers selected so as to include third reactive groups that are reactive with the second reactive groups displayed by the nanoparticles. In still another embodiment, a kit includes a set of nanoparticles derivatized with first half-linkers and a set of second half-linkers derivatized with one or more types of functional moiety. Such a kit can be employed by the user to attach the supplied second half-linkers and functional moieties, or the supplied functional moieties can be supplemented with one or more functional moieties supplied by the user.

Use of Functionalized Nanoparticles in Treatment and Diagnosis

Functionalized nanoparticles prepared according to a method of the invention can be used in the treatment and/or diagnosis of a variety of medical conditions, including neoplastic diseases infectious diseases, and chronic diseases. Any medical condition or disease can be treated or diagnosed using the functionalized nanoparticles provided that a cellular, intracellular, or molecular target specific for the condition is known. The functionalized nanoparticles can be particularly useful in diagnosis because of their unique ability to precisely target to cells, cellular compartments, or tissues bearing specific molecules or combinations of molecules, given that multiple delivery and/or effector groups can be attached, as well as one or more tracking (e.g., imaging) moieties. Their powerful targeting ability and ability to concentrate in mitochondria renders these functionalized nanoparticles also very effective at treating cancer, where they can be used to selectively kill tumor cells.

Any dose protocol or route of administration consistent with the access of the functionalized nanoparticles to their target is within the scope of the invention. The therapeutic compositions of the invention may be administered orally, topically, or parenterally (e.g., intranasally, subcutaneously, intramuscularly, intravenously, or intra-arterially) by routine methods in pharmaceutically acceptable inert carrier substances. For example, the compositions of the invention may be administered in a sustained release formulation using a biodegradable biocompatible polymer, or by on-site delivery using micelles, gels or liposomes. The functionalized nanoparticles can be administered in a dosage of 0.25 µg/kg/day to 5 mg/kg/day, and preferably 1 µg/kg/day to 500 µg/kg/day. Optimal dosage and modes of administration can readily be determined by conventional protocols.

The therapeutic compositions of the invention can be administered independently or co-administered with another agent.

The examples described herein are provided to illustrate advantages of the invention, including those that have not been previously described, and to further assist a person of ordinary skill in the art with using the methods of the invention. The examples can include or incorporate any of the variations or inventive embodiments as described herein. The embodiments that are described herein also can each include or incorporate the variations of any or all other embodiments of the invention. The following examples are not intended in any way to otherwise limit or otherwise narrow the scope of the disclosure as provided herein.

The following examples are presented to illustrate the advantages of the present invention and to assist one of ordinary skill in making and using the same. These examples are not intended in any way otherwise to limit the scope of the disclosure.

EXAMPLES

Example 1

Preparation of First Half-Linkers

Two series of terminally functionalized thiolated units were prepared for use as first half-linkers. In each series lipoic acid was used as the dithiolated component (dithiol group serving as the first reactive group). In the first series, lipoic acid was attached to commercially available α-amino-ω-azido oligoethylene glycols (n=3, 5, 7, 9) using standard peptide coupling methods (N-hydroxysuccinimide, dicyclohexylcarbodiimide, DMF) in isolated yields of 60-85%. Increasing the ethylene glycol content created more polar, hydrophilic compounds. In the second series, an oligoethylene glycol was sequentially alkylated with propargyl or allyl bromide, converted to terminal amino derivative (Mitsunobu reaction with phthalimide followed by hydrazinolysis) and coupled to lipoic acid as described above. The resulting compounds provided first half-linkers of variable length and having various second reactive groups.

Example 2

Ligation of Ethynylated Functional Moieties to First Half-Linkers

Several commercially available ethynylated steroid compounds, including 17α-ethynyl testosterone, 17α-ethynylnontestosterone and 17α-ethynyl estradiol, were selected as effector compounds to demonstrate the ligation methods. Ethynylated derivatives of fluorescein and 4-amino-TEMPO were also prepared for use as imaging agents. An ethynylated derivative of the 4-anilinoquinazoline EGFR tyrosine kinase inhibitor Tarceva® (erlotinib, which is N-(3-ethynylphenyl)-6,7-bis(2-methoxyethoxy)quinazolin-4-amine) was also prepared. In addition, an azido-oligoethylene glycolated-11β-substituted (antiestrogenic) steroid was prepared. The syntheses of the tyrosine kinase inhibitor and the anti-estrogen were based on a computational analysis of the crystal structures of inhibitors/ligands with their target proteins. Ligation of several lipoamido-azido derivatives (first half-linker) with ethynylated functional moieties (fluorescein and steroids) (second half-linker) were carried out using the Huisgen [3+2] cycloaddition reaction. The yields of product were at least 30-50%.

Example 3

Coupling of a First Half-Linker to Nanoparticles

Careful reduction of gold nanoparticles with borohydride in the presence of lipoic acid yielded dithiolated gold nanoparticles with diameters ranging from 15-25 nm. Initial preparation of nanoparticles using a dithiolated azido-oligoethylene glycol first half-linker (see above) also yielded materials with comparable dimensions. The nanoparticles were characterized using TEM and SEM to determine the particle diameter.

Example 4

Preparation of Functionalized Nanoparticles for Treatment of Prostate Cancer

Figure 7:
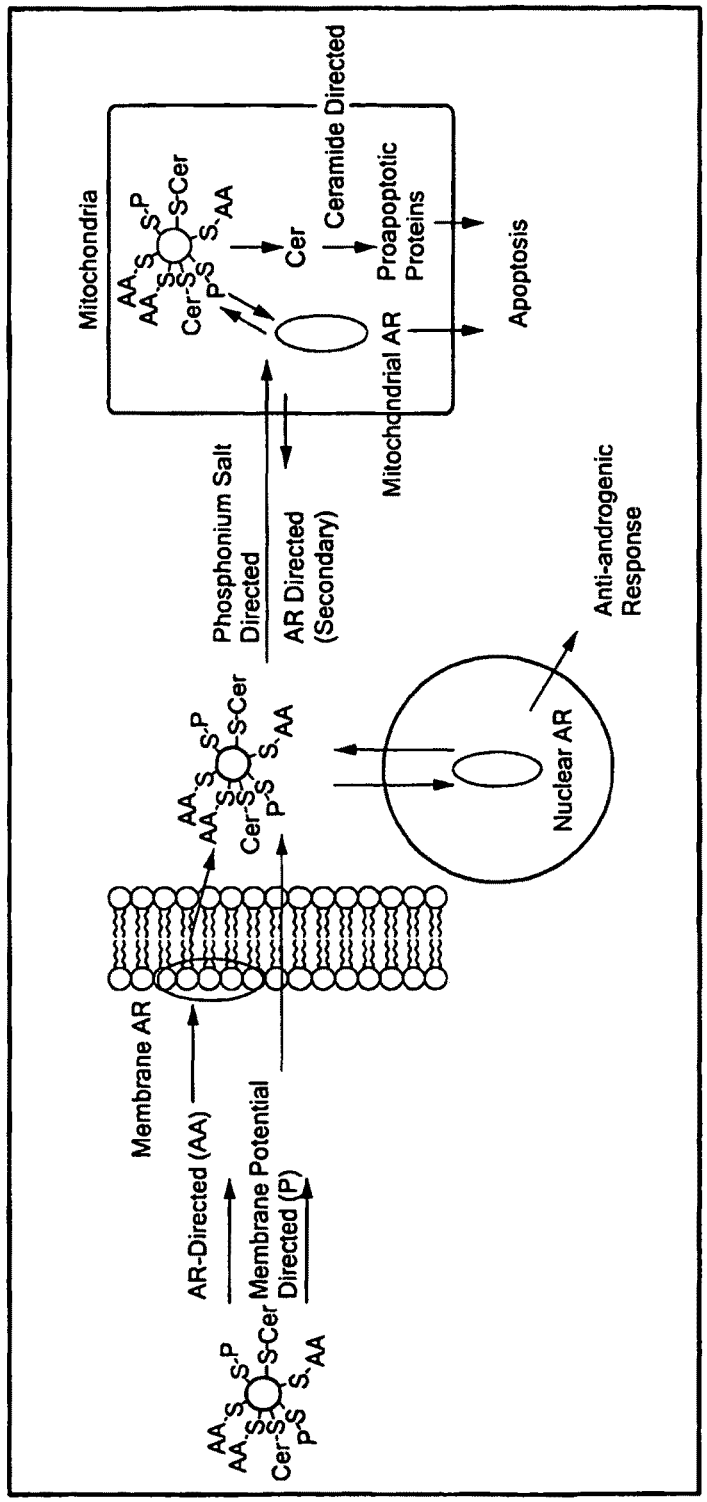
FIG. 7 illustrates the targeting strategy carried out by an embodiment of multifunctional gold nanoparticle designed to treat prostate cancer. AA represents an antagonist of both plasma membrane and nuclear androgen receptors. Cer represents a pro-apoptotic ceramide derivative. P represents a phosphonium derivative.

Multi-functional gold nanoparticles are prepared with tethered anti-androgen (AA) effector moieties that target the membrane androgen receptor (AR) for extracellular targeting and target the mitochondrial AR for intracellular therapy. The nanoparticles are also equipped with tethered phosphonium salts (PS) as deliver moiety for permeation through plasma membrane and localization with the mitochondria. As a further effector moiety, tethered, pH-cleavable ceramide derivatives (Cer) are added to the nanoparticles for mitochondrial induction of apoptosis. See FIG. 7. The nanoparticles induce apoptosis selectively in prostate cancer cells that over-express AR, but not in normal cells or cells that do not overexpress AR. The presence of leakier vasculature in tumors causes the nanoparticles to demonstrate preferential distribution (enhanced permeability and retention) within tumors compared to normal tissue. Accumulation is further enhanced by binding to the membrane AR, and internalization within cells is stimulated by the phosphonium cations. Within the target cells, mitochondrial uptake and retention are provided by the mitochondriotropic phosphonium cations and the antiandrogenic groups. Within the mitochondria, the low pH induces cleavage of the acyl hydrazone containing-ceramide derivative, inducing apoptosis, which is complemented by the anti-estrogenic response with the mitochondrial ER. Within the cytoplasmic and nuclear compartments, the presence of the AA groups may also exert secondary antiandrogenic responses. Normal tissues that do not have altered permeability do not accumulate nanoparticles as well, while normal cells that have unaltered membrane potentials and/or normal AR expression will demonstrate less nanoparticle uptake and retention.

Example 5

Animal Model for Testing Functionalized Nanoparticles in Treatment of Cancer

The efficacy of functionalized nanoparticles designed to target to tumor cells for cancer therapy or diagnosis is evaluated using xenografts in SCID mice. Non-prostate tumor cells are transplanted in one flank as a control, and prostate tumor cells (either AR-positive or AR-negative) are transplanted into the contralateral flank. Initially a single dose of functionalized nanoparticles is used, and their localization in the tumors is determined using the imaging properties of the nanoparticles (e.g., using a radiolabeled anti-androgen as tracking moiety). The efficacy of the targeting system in enhancing uptake in prostate vs. nonprostate tumors and AR-positive vs AR-negative tumors is evaluated. Based on the results, dose-response studies are undertaken to evaluate dose-related tumor responses (e.g., tumor shrinkage as a function of the dose of nanoparticles administered), with and without hormone deprivation.

Example 6

Figure 8:
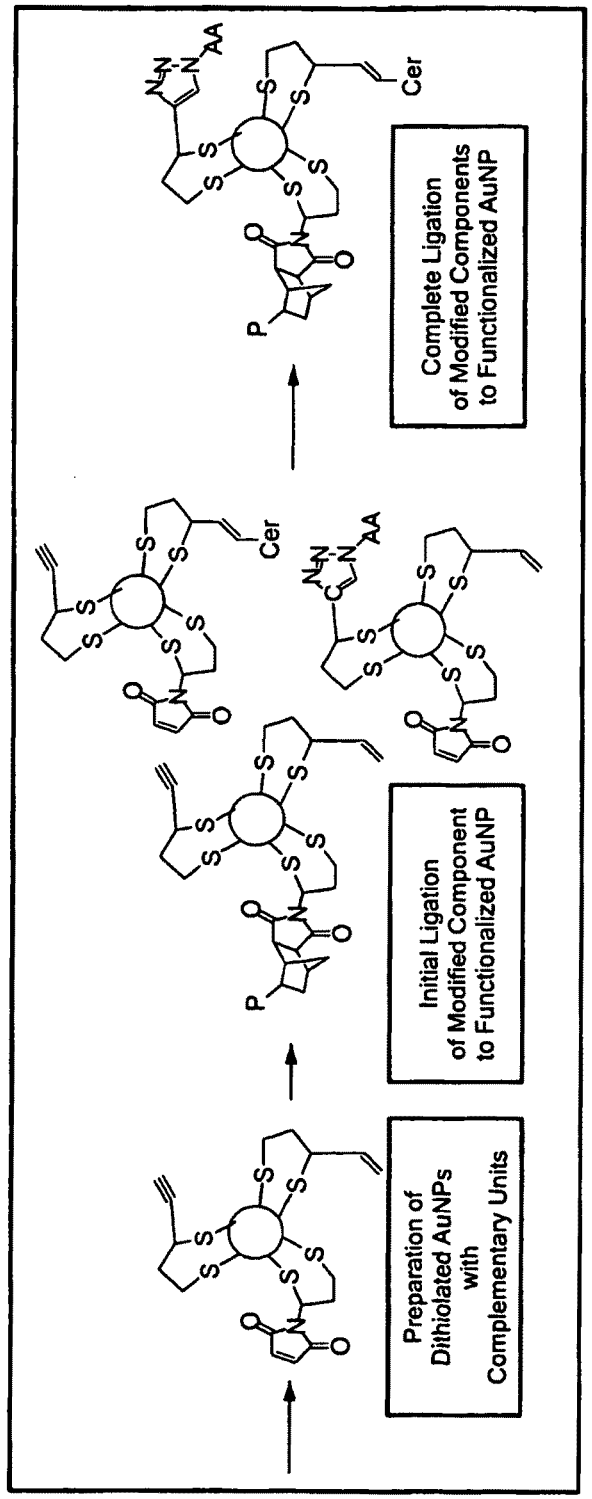
FIG. 8 illustrates an embodiment of a process for coupling a gold nanoparticle having a set of attached first half-linkers to a set of second half-linkers with functional moieties to form a completed multivalent functionalized nanoparticle.

Coupling of Functional Moieties to First Half-Linkers Using Chemo-Orthogonal Reactions Functionalized gold nanoparticles are prepared having three different first half-linkers, as indicated at the left-hand side of FIG. 8. Three different derivatized functional moieties are added. An azido antiandrogen (AA) is attached using Huisgen-3+2 cycloaddition ("click" chemistry) to generate a triazole. An alkenyl ceramide (Cer) is added using the ruthenium Grubbs' catalysts to generate a biologically stable trans alkene. A phosphonium salt (P) is added using the Diels-Alder cyclization to generate a bicyclic derivative. These ligation reactions are orthogonal.

Use

Figure 9:
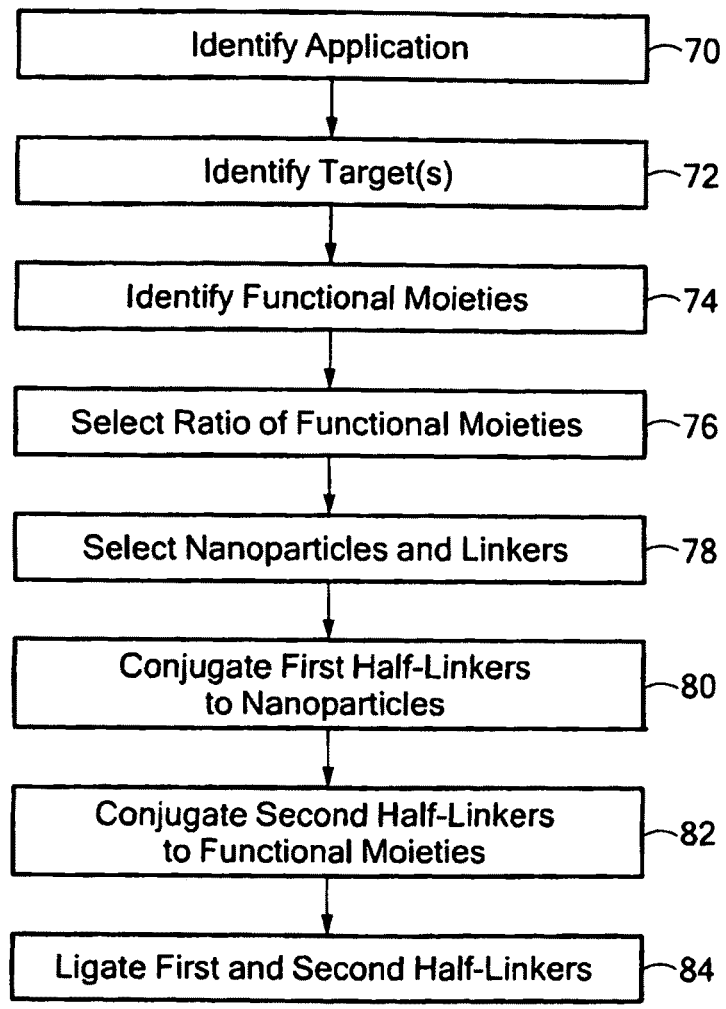
FIG. 9 is a flow chart of one overall approach to designing and fabricating multivalent functionalized nanoparticles.

FIG. 9 shows a flow chart of one possible scheme for designing and preparing functionalized nanoparticles for medicinal use. The first step (70) is to identify the use of the functionalized nanoparticles. This defines the cell type that will be the target or contain molecular targets for the nanoparticles. The second step (72) is to identify the specific molecular targets or cell compartments that the nanoparticles will be directed to. The third step (74) is the identification of the functional moieties to be installed on the nanoparticles. This is determined based on the receptors, over/underexpressed proteins, lipids, carbohydrates, membrane penetration mechanisms, mitochondrial targets, nuclear targets, and application (delivery moieties, tracking moieties) intended for the nanoparticles. In the fourth step (76), the ratio (composition stoichiometry) of the selected functional moieties is decided upon. This is based on the relative needs for each moiety to function. For example, a therapeutic agent (e.g., ceramide derivative) must be released from endosomes or mitochondria via a pH-sensitive cleavage and might be in the highest ratio. Steroids or other receptor ligands often must recognize membrane receptors via multivalent interactions, but do not need to be cleaved, and therefore might be present at the second highest ratio. Phosphonium salts direct nanoparticles via an electrochemical gradient, are not cleaved, and could be in the third highest ratio. Fluorescent groups do not need to be cleaved and can be present in lowest abundance. Ratios can define the type of ligation chemistry, and therefore determine the choice of complementary modules. For example, "click" chemistry (alkyne) with a pH releasable linker for a ceramide derivative might be the first attachment, Grubbs and thiol ligation chemistry for steroid and phosphonium salt the second. Next (78) the type of nanoparticles is determined; this can be determined by the end use, and in turn can determine the chemistry of the linkers. Gold, CLIO, or organic nanoparticles can be used in humans, or animals, or for other research purposes. Quantum dots might be undesirable for human use. In the next step (80) the first half-linkers are conjugated to the nanoparticles. Then the second half-linkers are conjugated to the functional moieties (82), and finally the first and second half-linkers are ligated (84). Certain incompatible combinations or coupling methods are to be avoided. For example, different chemoreactive groups cannot be available simultaneously on the nanoparticles during a given ligation method. G rubbs cross metathesis will react with both alkyne and alkene groups, so the alkynes will need to be ligated first. Carboxy and amino reactive groups cannot be present simultaneously on the same nanoparticle, since amide bonds would form between them instead of with the application module. Azides and alkynes cannot be present simultaneously on the same nanoparticle. Click chemistry would result in triazole formation between adjacent linker modules. Also, thiol addition and amide bond formation should occur in the latter stages because their ligations are the least stable, compared to triazoles and alkenes.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A set of functionalized nanoparticles for the diagnosis or treatment of a medical condition, each nanoparticle comprising two or more distinct sets of functional moieties, each set of functional moieties comprising a distinct functional moiety covalently attached to the nanoparticle by a distinct linker, wherein each linker comprises a first half-linker and a second half-linker; wherein the first half-linker is covalently bound to the nanoparticle through a first reactive group on the first half-linker, and is covalently bound to a third reactive group on the second half-linker through a second reactive group on the first half-linker, and the second half-linker is covalently bound to the functional moiety through a fourth reactive group on the second half-linker; wherein the second reactive group and third reactive group react as a cross-reacting pair to form the linker; and wherein each set of functional moieties comprises a distinct cross-reacting pair of second and third reactive groups, wherein the functional moieties are selected from the group consisting of a tracking moiety, a delivery moiety, and an effector moiety; and wherein said distinct functional moieties are present on the nanoparticles in a compositional stoichiometry whose variance is less than 5% over the set of functionalized nanoparticles.

2. The set of functionalized nanoparticles of claim 1 comprising a tracking moiety, wherein the tracking moiety is selected from a fluorophore, a 2,2,6,6-tetramethylpiperidine-1-oxyl (TEMPO) group, a perdeuterated alkyl or aryl phosphonium group, and a radioactive label.

3. The set of functionalized nanoparticles of claim 1 comprising a delivery moiety, wherein the delivery moiety is selected from the group consisting of an acid-labile group, an alkyl or aryl phosphonium group, a cell penetration group, a polyethylene glycol group, a receptor ligand, an antibody, and a polypeptide.

4. The set of functionalized nanoparticles of claim 1 comprising an effector moiety, wherein the effector moiety is selected from the group consisting of a receptor ligand, an antibody, an enzyme inhibitor, a polypeptide, a trigger of apoptosis, a drug, and a toxin.

5. The set of functionalized nanoparticles of claim 4, wherein the effector moiety is a receptor ligand selected from the group consisting of an estrogen receptor antagonist, an androgen receptor antagonist, folic acid, an RGD peptide, and tumor necrosis factor.

6. The set of functionalized nanoparticles of claim 4, wherein the effector moiety is an enzyme inhibitor which inhibits a tyrosine kinase.

7. The set of functionalized nanoparticles of claim 4, wherein the effector moiety is a trigger of apoptosis selected from the group consisting of ceramide, betulinic acid, and lonidamine.

8. The set of functionalized nanoparticles of claim 1, wherein the nanoparticles are selected from the group consisting of gold nanoparticles, silver nanoparticles, cross-linked iron oxide nanoparticles, silica nanoparticles, organic nanoparticles, and quantum dots.

9. The functionalized nanoparticles of claim 1, where the nanoparticles have an average diameter in the range from about 1 to about 100 nm.

10. The functionalized nanoparticles of claim 9, where the nanoparticles have an average diameter in the range from about 5 to about 20 nm.

11. The set of functionalized nanoparticles of claim 1, wherein the medical condition is selected from the group consisting of a neoplastic disease, an infectious disease, and a chronic disease.

12. The set of functionalized nanoparticles of claim 1, wherein each nanoparticle of the set comprises three or more different functional moieties.

13. A method of treating a medical condition, the method comprising administering to a subject the set of functionalized nanoparticles of claim 1.

14. A method of diagnosing a medical condition, the method comprising administering to a subject the set of functionalized nanoparticles of claim 1 and monitoring the results.

15. A method of delivering a chemical or biological agent to a cell, the method comprising contacting the cell with the set of functionalized nanoparticles of claim 1.

16. A kit for preparing the set of functionalized nanoparticles of claim 1, the kit comprising:

(a) a plurality of nanoparticles covalently bound to a set of first half-linkers through a first reactive group of the first half-linker, each first half-linker comprising a second reactive group;

(b) a set of second half-linkers covalently bound to a set of functional moieties and comprising a third reactive group, the set of functional moieties comprising two or more different types of functional moiety selected from the group consisting of a tracking moiety, a delivery moiety, and an effector moiety; wherein the set of first half-linkers comprises two or more different types of second reactive group and the set of second half-linkers comprises two or more different types of third reactive group, each type of second reactive group reacting with essentially only one type of third reactive group to form a cross-reacting pair.

17. A kit for preparing the set of functionalized nanoparticles of claim 1, the kit comprising:

(a) a plurality of nanoparticles covalently bound to a set of first half-linkers through a first reactive group of the first half-linker, each first half-linker comprising a second reactive group;

(b) a set of second half-linkers, each comprising a third reactive group and a fourth reactive group;

(c) a set of functional moieties, the set comprising two or more different types of functional moiety selected from the group consisting of a tracking moiety, a delivery moiety, and an effector moiety; wherein each functional group reacts with a fourth reactive group, and wherein the set of first half-linkers comprises two or more different types of second reactive group and the set of second half-linkers comprises two or more different types of third reactive group, each type of second reactive group reacting with essentially only one type of third reactive group to form a cross-reacting pair.

18. A kit for preparing the set of functionalized nanoparticles of claim 1, the kit comprising:

(a) a plurality of nanoparticles covalently bound to a set of first half-linkers through a first reactive group of the first half-linker, each first half-linker comprising a second reactive group;

(b) a set of second half-linkers, each comprising a third reactive group and a fourth reactive group; wherein the fourth reactive group is capable of reacting with a set of user-supplied functional moieties, the set comprising two or more different types of functional moiety selected from the group consisting of a tracking moiety, a delivery moiety, and an effector moiety; and wherein the set of first half-linkers comprises two or more different types of second reactive group and the set of second half-linkers comprises two or more different types of third reactive group, each type of second reactive group reacting with essentially only one type of third reactive group to form a cross-reacting pair.

19. A composition comprising two or more sets of functionalized nanoparticles according to claim 1, wherein each set comprises one or more delivery moieties not found in the other sets.

20. A composition comprising two or more sets of functionalized nanoparticles according to claim 1, wherein each set comprises one or more effector moieties not found in the other sets.

21. The set of functionalized nanoparticles of claim 1, wherein each nanoparticle has a first functional moiety attached to the nanoparticle by a first linker and a second functional moiety attached to the nanoparticle by a second linker, wherein the first and second linkers have distinct pairs of second and third reactive groups selected, respectively, from the group consisting of: an azide and an alkyne; an alkene and an alkene; a maleimide and either a dienyl or a thiol; an alcohol and a phenol; and an amine and a carboxylic acid.

22. The set of functionalized nanoparticle of claim 21, wherein the second and third reactive groups of the first linker are, respectively, an azide and an alkyne.

23. The set of functionalized nanoparticle of claim 21, wherein the second and third reactive groups of the first linker are, respectively, an alkene and an alkene.

24. The set of functionalized nanoparticle of claim 21, wherein the second and third reactive groups of the first linker are, respectively, a maleimide and either a dienyl or a thiol.

25. The set of functionalized nanoparticle of claim 21, wherein the second and third reactive groups of the first linker are, respectively, an alcohol and a phenol.

26. The set of functionalized nanoparticle of claim 21, wherein the second and third reactive groups of the first linker are, respectively, an amine and a carboxylic acid.

* * * * *